US005877215A

United States Patent [19]
McClay et al.

[11] Patent Number: 5,877,215
[45] Date of Patent: Mar. 2, 1999

[54] METHOD OF TREATING NEOPLASTIC CELLS WITH PROSTAGLANDIN AND RADIATION TREATMENT OR PROSTAGLANDIN AND PLATINUM-BASED ANTI-TUMOR AGENTS

[75] Inventors: Edward F. McClay, Folly Beach; Sebastiano Gattoni-Celli, Mt. Pleasant; Joseph M. Jenrette, III, Charleston, all of S.C.

[73] Assignee: Medical University of South Carolina, Charleston, S.C.

[21] Appl. No.: 619,854

[22] Filed: Mar. 20, 1996

[51] Int. Cl.$^6$ ........................ A61K 31/19; A61K 31/557; A61N 5/00
[52] U.S. Cl. ................................. 514/573; 600/1
[58] Field of Search ................................. 514/573; 600/1

[56] References Cited

PUBLICATIONS

McClay, E.F., Winski, P.J., Jones, J.A., Jenrette, III, J.M., Gattoni–Celli, S. "$\Delta^{12}$–Prostaglandin J$_2$ is cytotoxic alone and synergizes in combination with both cisplatin and radiation in human malignancies" Abstract #2696, Proceedings of the Am. Assoc. for Cancer Research vol. 37, p. 395, Mar. 1996.

Lee, Jeong–Hwa, Kim, Ho–Shik, Jeong Seong–Yun, Kim, In–Kyung "Induction of p53 and apoptosis by $\Delta^{12}$–PGJ$_2$ in human hepatocarcinoma SK–HEP–1 cells" FEBS Letters 368:348–352, Feb. 1995.

McClay, E.F., Albright, K.A., Jones, J.A., Christen, R., and Howell, S.B. "Tamoxifen delays the development of resistance to cisplatin in human malanoma and ovarian cancer cell lines", Br. J. Cancer, 70: 449–452, 1994.

McClay, E.F., Albright, K.A., Jones, J.A., Christen, R., and Howell, S.B. "Tamoxifen modulation of cisplatin sensitivity in human malignant melanoma cells", Cancer Res., 53: 1571–1576, Apr. 1, 1993.

Kim, I.K., Lee, J.H., Sohn, H.W., Kim, H.S., and Kim, S.H. "Prostaglandin A$_2$ and $\Delta^{12}$–prostaglandin J$_2$ induce apoptosis in L1210 cells", Fed Europ Biochem Soc, 321: 209–214, Apr. 1993.

Sasaguri, T., Masuda, J., Shimokada, K., Yokoto, T., Kosaka, C., Fujishima, M., and Ogata, J. "Prostaglandins A and J arrest the cell cycle of cultured vascular smooth muscle cells without suppression of c–myc expression", Exp. Cell Res., 200: 351–357, 1992.

Fukushima, M. "Biological activities and mechanisms of action of PG J$_2$ and related compounds: an update", Prostagl, Leukotri. Essen. Fatty Acids, 47: 1–12, 1992.

Choi, A.M.K., Fargnoli, J., Carlson, S.G., and Holbrook, N.J. "Cell growth inhibition by prostaglandin A$_2$ results in elevated expression of gadd153 mRNA", Exp. Cell Res., 199: 85–89, 1992.

Santoro, M.G., Garaci, E., and Amici, C. "Induction of heat shock protein synthesis by prostaglandis with antineoplastic and antiviral activity", Adv. prostaglandin, Thromboxane, and Leukotriene Res. 21:867–874, 1990.

Fornace, A.J., Nebert, D.W., Hollander, C., Luethy, L.D., Papthanasiou, M., Fargnoli, J., and Holbrook, N.J. "Mammalian genes coordinately regulated by growth arrest signals and DNA–damaging agents", Mol. Cell. Bio., 9: 41906–44203, Nov. 1989.

Santoro, M.G., Garaci, E., and Amici, C. "Prostaglandins with antiproliferative activity induce the synthesis of a heat shock protein in human cells", Proc. Natl. Acad. Sci., 86: 8407–8411, Nov. 1989.

Ohno, K., Fukushima, M., Fujiwara, M., and Narunmiya, S. "Induction of 68,000–dalton heat shock proteins by cyclopentenone prostaglandins", J. Bio. Chem., 263: 19764–19770, Dec. 25, 1988.

Hirata, Y., Hayashi, H., Ito, S., Kikawa, Y., Ishibashi, M., Sudo, M., Miyazaki, H., Fukushima, M., Narumiya, S., and Hayaishi, O. "Occurrence of 9–deoxy–$\Delta^9$, $\Delta^{12}$–13, 14–dihydroprostaglandin D$_2$ in human urine", J. Biol. Chem., 263: 16619–16625, 1988.

Kato, T., Fukushima, M., Kurozumi, S., and Noyri, R. "Antitumor activity of $\Delta^7$–prostaglandin A$_1$, and $\Delta^{12}$–prostaglandin J$_2$ in vitro and in vivo", Cancer Res., 46: 3538–3542, Jul. 1986.

Kikuchi, Y., Myiauchi, M., Oomori, K., Kita, T., Kizawa, I., and Kato, K. "Inhibition of ovarian cancer cell growth in vitro and in nude mice by prostaglandin D$_2$", Cancer Res., 46:3364–3366, Jul. 1986.

Bhuyan, B.K., Adams, E.G., Badiner, G.J., Li, L.H., and Barden, K. "Cell cycle effects of Prostaglandins A$_1$, A$_2$ and D$_2$ in human murine melanoma cells in culture", Cancer Res., 46: 1688–1693, Apr. 1986.

Heavey, D.J., Lumley, P., Barrow, S.E., Murphy, M.B., Humphrey, P.P.A., and Dollery, C.T. "Effects of intravenous infusions of prostaglandin D$_2$ in man", Prostaglandins, 28: 755–767, Dec. 1984.

(List continued on next page.)

Primary Examiner—Jerome D. Goldberg
Attorney, Agent, or Firm—Needle & Rosenberg, P.C.

[57] ABSTRACT

The invention is directed to a method of increasing ionizing radiation's cytotoxic effects on a neoplasm in a subject by increasing the neoplasm's sensitivity to ionizing radiation, comprising administering a therapeutically effective amount of prostaglandin to the subject, and subjecting the neoplasm to a therapeutically effective amount of ionizing radiation, thereby increasing the cytotoxic effects of the ionizing radiation on the neoplasm. The invention is further directed to a method of reducing the therapeutically effective amount of ionizing radiation required to treat a neoplasm in a subject, compared to treating with ionizing radiation alone, comprising administering a therapeutically effective amount of prostaglandin to the subject, thereby reducing the therapeutically effective amount of ionizing radiation required to treat the neoplasm in the subject, compared to treating with ionizing radiation alone, and subjecting the neoplasm in the subject to the reduced therapeutically effective amount of ionizing radiation. The invention is also directed to a method of treating a neoplasm in a subject, comprising administering a therapeutically effective amount of prostaglandin and administering a therapeutically effective amount of cisplatin to the subject, wherein the therapeutically effective amount of the platinum-based anti-tumor agent is less than 60 mg/meter$^2$.

19 Claims, 3 Drawing Sheets

OTHER PUBLICATIONS

Barrow, S.E., Heavey, D.J., Ennis, M., Chappell, CG., Blair, I.A., and Dollery, C.T. "Measurement of prostaglandin $D_2$ and identification of metabolities in human plasma during intravenous infusion", *Prostaglandins* 28(6):743–753, Dec. 1984.

Kikawa, Y., Narumiya, S., Fukushima, M., Wakatsuka, H., and Hayaishi, O. "9–Deoxy–$\Delta^9$, $\Delta^{12}$–13,14–dihydroprostaglandin $D_2$, a metabolite of prostaglandin $D^2$ formed in human plasma", *Proc. Natl. Acad. Sci.*, 81: 1317–1321, Mar. 1984.

Fitzpatrick, F.A. and Wynalda, M.A. "Albumin catalyzed metabolism of prostaglandin $D^2$: Identification of products formed in vitro", *J. Biol. Chem.*, 258: 11713–11718, Mar. 25, 1983.

Simmet, T. and Jaffe, B.M. Inhibition of B–16 melanoma growth in vitro by prostagland in $D_2$ *Prostaglandins*, 25: 47–54, Jan. 1983.

Fukushima, M., Kato, T., Ota, K., Arai, Y., Narumiya, S., and Hayaishi, O. "9–deoxy–$\Delta^9$–prostaglandin $D_2$, a prostaglandin $D_2$ derivative with potent antineoplastic activity and weak smooth muscle–contracting activities", *Biochem. Biophy. Res. Comm.*, 109: 626–633, Dec. 15, 1982.

Stringfellow, D.A. and Fitzpatrick, F.A. "Prostaglandin $D_2$ controls metastasis of malignant melanoma cells", *Nat.*, 282: 76–78, Nov. 1979.

Fitzpatrick, F.A. and Stringfellow, D.A. "Prostaglandin $D_2$ formation by malignant melanoma cells correlates inversely with cellular metastatic potential", *Proc. Natl. Acad. Sci.*, 76: 1765–1769, Apr. 1979.

See–Lasley et al., Manual of Owcology Therapeutics, C.U.Mosby Co., StLouis, 1981, pp. 17,88,404.

METHOD OF TREATING NEOPLASTIC CELLS WITH PROSTAGLANDIN AND RADIATION TREATMENT OR PROSTAGLANDIN AND PLATINUM-BASED ANTI-TUMOR AGENTS

BACKGROUND OF THE INVENTION

1. Field of the Invention

This invention relates generally to a method of treating neoplastic cells with prostaglandin. More particularly, a therapeutically effective amount of ionizing radiation required to treat a neoplasm in a subject can be reduced by administering prostaglandin to the subject. In another embodiment, the present invention relates to treating a neoplasm in a subject by administering to the neoplasm a therapeutically effective amount of prostaglandin and a therapeutically effective amount of cisplatin.

2. Background Art

Treatment of neoplasms often requires the use of ionizing radiation to kill or halt the growth of neoplastic cells. In that respect, ionizing radiation has proven valuable as a tool for clinical diagnosis and radiotherapy. Exposing a subject to ionizing radiation, however, has the inherent risk of injuring or killing surrounding normal cells, inducing mutations, or even producing latent cancers. Any technique for treating a neoplasm in a subject which can decrease the therapeutically effective dose of ionizing radiation necessary to treat the neoplastic cells will be important in order to reduce the chances of causing damage to the subject. The present invention provides such a method of reducing the effective dose of ionizing radiation necessary to treat a neoplasm by administering to the neoplastic cells a prostaglandin. In addition, in another embodiment of the invention, the use of prostaglandin provides for a reduction in the amount of a platinum-based anti-tumor agent to treat a neoplasm.

SUMMARY OF THE INVENTION

In accordance with the purpose(s) of this invention, as embodied and broadly described herein, this invention, in one aspect relates to a method of treating a neoplasm in a subject, comprising administering a therapeutically effective amount of prostaglandin to the subject, and subjecting the neoplasm to a cytotoxic amount of ionizing radiation, thereby treating the neoplasm.

The invention further provides a method of increasing ionizing radiation's cytotoxic effects on a neoplasm in a subject by increasing the neoplasm's sensitivity to ionizing radiation, comprising administering a therapeutically effective amount of prostaglandin to the subject, and subjecting the neoplasm to a therapeutically effective amount of ionizing radiation, thereby increasing the cytotoxic effects of the ionizing radiation on the neoplasm.

In another aspect, the invention provides a method of reducing the therapeutically effective amount of ionizing radiation required to treat a neoplasm in a subject, compared to treating with ionizing radiation alone, comprising administering a therapeutically effective amount of prostaglandin to the subject, thereby reducing the therapeutically effective amount of ionizing radiation required to treat the neoplasm in the subject, compared to treating with ionizing radiation alone, and subjecting the neoplasm in the subject to the reduced therapeutically effective amount of ionizing radiation.

In another aspect, the invention provides a method of screening a prostaglandin compound's capacity to increase ionizing radiation's cytotoxic effect upon neoplastic cells, comprising combining the prostaglandin compound and the neoplastic cells, subjecting the neoplastic cells to an amount of ionizing radiation, and determining viability of the neoplastic cells, a prostaglandin compound which decreases the viability of the neoplastic cells indicating a compound with a capacity to increase ionizing radiation's cytotoxic effect upon neoplastic cells.

In another aspect, the invention provides a method of treating a neoplasm in a subject, comprising administering a therapeutically effective amount of prostaglandin and administering a therapeutically effective amount of a platinum-based anti-tumor agent to the subject, wherein the therapeutically effective amount of the platinum-based anti-tumor agent is less than 60 mg/meter$^2$.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying figures, which are incorporated in and constitute a part of this specification, illustrate several embodiments of the invention and together with the description, serve to explain the principles of the invention.

DETAILED DESCRIPTION OF THE INVENTION

Figure 1:
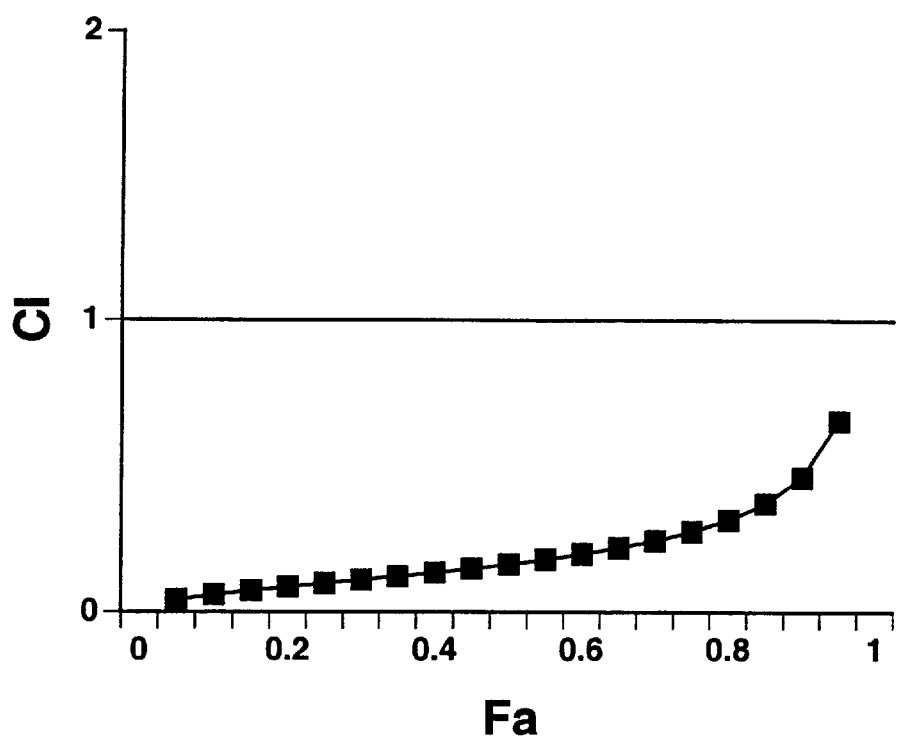
FIG. 1 shows the median effects analysis plot of the interaction between $\Delta^{12}$-PG J$_2$ and cisplatin (DDP) in the human melanoma cell line 289 TAM$_{(6)}$. FA=the fraction affected (the fraction of cells killed by $\Delta^{12}$-PG J$_2$). CI=the combination index (the interaction between $\Delta^{12}$-PG J$_2$ and DDP; CI values above 1 indicate an antagonistic effect, CI values=1 indicate an additive effect, and CI values below 1 indicate a synergistic effect).

The present invention may be understood more readily by reference to the following detailed description of preferred embodiments of the invention and the Example included therein and to the Figures and their previous and following description.

Before the present methods and compositions are disclosed and described, it is to be understood that this invention is not limited to specific methods or other specific compositions, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a neoplasm" includes multiple neoplasms.

In one aspect, the invention relates to a method of treating a neoplasm in a subject, comprising administering a therapeutically effective amount of prostaglandin to the subject, and subjecting the neoplasm to a cytotoxic amount of ionizing radiation, thereby treating the neoplasm.

The invention further provides a method of increasing ionizing radiation's cytotoxic effects on a neoplasm in a subject by increasing the neoplasm's sensitivity to ionizing radiation, comprising administering a therapeutically effective amount of prostaglandin to the subject, and subjecting the neoplasm to a therapeutically effective amount of ionizing radiation, thereby increasing the cytotoxic effects of the ionizing radiation on the neoplasm.

The neoplastic cell's sensitivity to ionizing radiation can relate to the ability of the ionizing radiation to induce apoptotic cell death, often the result of damage to the cell's DNA. Administering prostaglandin to the neoplasm can decrease the amount of ionizing radiation needed to induce apoptotic cell death, thereby increasing the neoplastic cell's sensitivity to the ionizing radiation. Therefore, a lower amount of ionizing radiation can be used to induce apoptotic cell death when prostaglandin is administered to the neoplastic cells. This then relates to the therapeutically effective amount of ionizing radiation required to treat a neoplasm being reduced as a result of administering to the neoplastic cells a therapeutically effective amount of prostaglandin. Alternatively, the amount of ionizing radiation used to treat a neoplasm in a subject may be kept constant relative to the amount typically used without also administering prostaglandin, and prostaglandin administered to the subject, thereby increasing the cytotoxic effect of the ionizing radiation.

In another aspect, the invention provides a method of reducing the therapeutically effective amount of ionizing radiation required to treat a neoplasm in a subject, compared to treating with ionizing radiation alone, comprising administering a therapeutically effective amount of prostaglandin to the subject, thereby reducing the therapeutically effective amount of ionizing radiation required to treat the neoplasm in the subject, compared to treating with ionizing radiation alone, and subjecting the neoplasm in the subject to the reduced therapeutically effective amount of ionizing radiation.

In another aspect, the invention provides a method of screening a prostaglandin compound's capacity to increase ionizing radiation's cytotoxic effect upon neoplastic cells, comprising combining the prostaglandin compound and the neoplastic cells, subjecting the neoplastic cells to an amount of ionizing radiation, and determining viability of the neoplastic cells, a prostaglandin compound which decreases the viability of the neoplastic cells indicating a compound with a capacity to increase ionizing radiation's cytotoxic effect upon neoplastic cells.

Viability of the treated neoplastic cells relates to the neoplastic cell's ability to live and capacity to replicate. For example, neoplastic cells can be grown in vitro and subjected to the screening method provided herein. The cells can then be assayed for their ability to form colonies, for their ability to exclude or uptake stains, or for their ability to incorporate molecules such as nucleotides, and the like. Aditionally, cell viability may be deterimied by conducting assays which evaluate apoptosis. For example, the formation of DNA fragments may be assayed by separation of DNA fragments on electrophoretic gels, or through immunoassays such as an enzyme-linked immunosorbent assay (ELISA). A skilled practitioner can readily appreciate the vast number of assays available to determine a cell's viability.

The term "neoplasm" is a term familiar to one of ordinary skill in the art and is used herein to describe an abnormal mass of tissue or cells. The growth of these tissues or cells exceeds and is uncoordinated with that of the normal tissues or cells and persists in the same excessive manner after cessation of the stimuli which evoked the change. These neoplastic tissues or cells show a lack of structural organization and coordination relative to normal tissues or cells which usually results in a mass of tissues or cells which can be either benign or malignant.

As used herein, neoplasm includes any neoplasm. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, and the like.

Treating a neoplasm includes, but is not limited to, halting the growth of the neoplasm, killing the neoplasm, or reducing the size of the neoplasm. Halting the growth of the neoplasm refers to halting any increase in the size of the neoplasm or the neoplastic cells, or halting the division of the neoplasm or the neoplastic cells. Reducing the size of the neoplasm relates to reducing the size of the neoplasm or the neoplastic cells.

The term "subject" as used herein refers to any target of the treatment. As provided herein in the Example and which is provided by the present invention, is a method of treating neoplastic cells which were grown in tissue culture. Also provided by the present invention is a method of treating neoplastic cells in situ, or in their normal position or location. For example, neoplastic cells of breast or prostate tumors. These in situ neoplasms can be located within or on a wide variety of hosts; for example, human hosts, canine hosts, feline hosts, equine hosts, bovine hosts, porcine hosts, and the like. Any host in which is found a neoplasm or neoplastic cells can be treated and is provided by the present invention.

Any of the prostaglandins known in the art can be used in the present invention. Prostaglandins are a class of biologically active lipids that are derived from arachidonic acid. These compounds are divided into types based on the structure of the substituted 5-membered carbon ring. For example, there are prostaglandin A-type molecules, prostaglandin B-type molecules, prostaglandin C-type molecules, prostaglandin D-type molecules, prostaglandin E-type molecules, prostaglandin F-type molecules, prostaglandin G-type molecules, prostaglandin H-type molecules prostaglandin I-type molecules, prostaglandin J-type molecules, and other types well known to those of skill in the art. There are also several members or species within each group. Examples of these species include, but are not limited to, prostaglandin $A_1$ ([13E,15S]-15-Hydroxy-9-oxoprosta-10, 13 -dien-1-oic acid), prostaglandin $A_2$ ([5Z,13E,15S]-15-Hydroxy-9-oxoprosta-5,10,13-trien-1-oic acid), prostaglandin $B_1$ ([13E, 15S]-15-Hydroxy-9-oxoprosta-8[12],13-dien-1-oic acid), prostaglandin $B_2$ ([5Z,13E,15 S]-15-Hydroxy-9-oxoprosta-5,8[12],13-trien-1-oic acid), prostaglandin $D_2$ ([5Z,9α,13E,15S]-15-Dihydroxy-11-oxoprosta-5,13-dien-1-oic acid), prostaglandin $E_1$ ([11α, 13E,15S]-11,15-Dihydroxy-9-oxoprost-13-enoic acid), prostaglandin $E_2$ ([5Z, 11α, 13E, 15S]- 11,15-Dihydroxy-9-oxoprosta-5,13-dienoic acid), prostaglandin $F_{1α}$ ([9α,11α, 13E, 15S]-9,11,15-Trihydroxy-9-oxoprost-13-en-1-oic acid), prostaglandin $F_{2α}$ ([5Z,9α,11α, 13E, 15S]-9,11,15-Trihydroxy-9-oxoprosta-5,13-dienoic acid), prostaglandin $I_2$ ([5Z,9α,11α,13E,15 S]-6,9-Epoxy-11,15-Dihydroxy-9-oxoprosta-5,13-dien-1-oic acid), prostaglandin $J_2$ ([5Z,13E, 15 S]-15-Hydroxy-11-oxoprosta-5,9,13-trien-1-oic acid), and $Δ^{12}$-prostaglandin J-2 (prosta-5,9,12-trien-1-olic acid, 15-hydroxy-11-oxo-). These compounds are commercially available through chemical companies such as Sigma Chemical Company (St. Louis, Mo.) and Cayman Chemicals (Ann Arbor, Mich.). Prostaglandins of the present invention also include derivatives, analogs, and isomers of the known prostaglandins.

The present invention provides for administering a therapeutically effective amount of prostaglandin to the subject and subjecting the neoplasm to a cytotoxic amount of ionizing radiation, thereby treating the neoplasm. A skilled practitioner in the art can readily determine the effective amount of the prostaglandin to administer and will depend on factors such as weight, size, the severity of the neoplastic condition, and the type of subject itself. The therapeutically effective amount can readily be determined by routine optimization procedures.

The administration of the therapeutically effective amount of prostaglandin to the subject can be a single administration or multiple administrations. Where the administrations are multiple and over a period of time, the amount of prostaglandin administered can range, for example, from about 1 ng to about 1 g/kg/day. In another embodiment, the amount of prostaglandin administered can range from about 5 ng/kg/day to about 500 mg/kg/day; in another embodiment, the amount of prostaglandin administered can range from about 10 ng/kg/day to about 250 mg/kg/day; in another embodiment, the amount of prostaglandin administered can range from about 10 ng/kg/day to about 100 mg/kg/day; in another embodiment, the amount of prostaglandin administered can range from about 10 ng/kg/day to about 50 mg/kg/day; in another embodiment, the amount of prostaglandin administered can range from about 10 ng/kg/day to about 25 mg/kg/day; in another embodiment, the amount of prostaglandin administered can range from about 10 ng/kg/day to about 10 mg/kg/day. Preferably, the amount of prostaglandin administered can range from about 10 ng/kg/day to about 1 mg/kg/day, and subranges between this amount, e.g. 10 ng/kg/day to about 500 µg/kg/day, 10 ng/kg/day to about 100 µg/kg/day, 100 ng/kg/day to about 500 µg/kg/day, 100 ng/kg/day to about 100 µg/kg/day, etc. Even more preferably, the amount of prostaglandin administered can range from about 300 ng/kg/day to about 3000 ng/kg/day.

A skilled practitioner in the art can readily determine the number of days or the period of time these multiple therapeutically effective amounts of prostaglandin are to be administered. For example, this period can range between 1 and 100 days; in another embodiment, the period can range from between 1 and 50 days; in another embodiment, this period can range from between 1 and 25 days; in another embodiment, this period can range from between 1 and 20 days; in another embodiment, this period can range from between 1 and 15 days; in another embodiment, this period can range from between 1 and 5 days; in another embodiment, this period can range from between 1 and 2 days. In another embodiment, this period can range from between 1 and 10 days.

The period of time these multiple therapeutically effective amounts of prostaglandin are to be administered is not limited to days. For example, the period can be determined as a period of hours, or even minutes. For example, this period can range between 1 and 48 hours; in another embodiment, this period can range from between 1 and 36 hours; in another embodiment, this period can range from between 1 and 24 hours; in another embodiment, this period can range from between 1 and 18 hours; in another embodiment, this period can range from between 1 and 12 hours; in another embodiment, this period can range from between 1 and 6 hours; in another embodiment, this period can range from between 1 and 3 hours; and in another embodiment, this period can range from between 1 and 2 hours. Preferably, the period of time that the therapeutically effective amounts of prostaglandin is administered is about 20 minutes.

Alternatively, the administration of the therapeutically effective amount of prostaglandin may be continuous. For example, a subject can be administered prostaglandin parenterall, such as intravenously. Alternatively, a subject can be administered prostaglandin orally, or as a suppository, or as an inhalant. Where the neoplastic cells are external, the cells may be administered prostaglandin continuously through a topical treatment, for example. Alternatively, where neoplastic cells are being cultured in vitro, the cells may be administered prostaglandin continuously by adding the prostaglandin to the culture medium.

Similarly, a skilled practitioner in the art can readily determine a cytotoxic amount of ionizing radiation. A cytotoxic amount is an amount which causes death of the target cells. Such amount should be the minimum amount to achieve death of the target cells while causing no or minimal damage to the surrounding tissues or cells. This amount can in part depend on the tissue or cell type, the location of the tissue or cells, the type of neoplastic condition, the type of ionizing radiation, the age of the tissue or cells, and the extent of the neoplastic condition. The cytotoxic amount of ionizing radiation can readily be determined by optimization procedures as well. In one embodiment, the amount of ionizing radiation can be reduced by about 75% by administering a therapeutically effective amount of prostaglandin.

The neoplasm can be subjected to the ionizing radiation in a single exposure or by multiple exposures. Where the exposure is a single exposure, the dose amount of ionizing radiation the neoplasm is subjected to can range from about 1 cGy (centigrays) to about 600 cGy; in another embodiment, the dose can range from about 1 cGy to about 500 cGy; in another embodiment, the dose amount can range from about 1 cGy to about 400 cGy; in another embodiment, the dose amount can range from about 1 cGy to about 300 cGy; and in another embodiment, the dose amount can range from about 1 cGy to about 200 cGy. Preferably, the dose amount can range from about 5 cGy to about 200 cGy, and subranges between this amount, e.g. 10 to 100 cGy, 10 to 150 cGy, 20 to 150 cGy, 25 to 125 cGy, and so on. Even more preferably, the dose amount can range from about 30 cGy to about 60 cGy. Even more preferably, the dose amount can be about 50 cGy.

Alternatively, the neoplasm can be subjected to the ionizing radiation by multiple exposures. Where the exposures are multiple, each dose amount of ionizing radiation the neoplasm is subjected to can range from about 1 cGy (centigrays) to about 600 cGy per day; in another embodiment, each dose can range from about 1 cGy to about 500 cGy per day; in another embodiment, each dose amount can range from about 1 cGy to about 400 cGy per day; in another embodiment, each dose amount can range from about 1 cGy to about 300 cGy per day; in another embodiment, each dose amount can range from about 1 cGy to about 200 cGy per day; in another embodiment, each dose amount can range from about 1 cGy to about 100 cGy per day; in another embodiment, each dose amount can range from about 1 cGy to about 75 cGy per day; in another embodiment, each dose amount can range from about 1 cGy to about 50 cGy per day; in another embodiment, each dose amount can range from about 1 cGy to about 25 cGy per day; and in another embodiment, each dose amount can range from about 1 cGy to about 10 cGy per day. Preferably, each dose amount can range from about 5 cGy to about 200 cGy per day, and subranges between this amount, e.g. 10 to 100 cGy per day, 10 to 150 cGy per day, 20 to 150 cGy per day, 100 to 125 cGy per day, and so on.

The type of ionizing radiation will be apparent to a skilled practitioner in the art. Any radiation where a nuclear particle has sufficient energy to remove an electron or other particle from an atom or molecule, thus producing an ion and a free electron or other particle, is contemplated. Examples of such ionizing radiation include, but are not limited to, gamma rays, X-rays, and alpha particles. Ionizing radiation is commonly used in medical radiotherapy and the specific techniques for such treatment will be apparent to a skilled practitioner in the art.

The neoplasm in a subject being treated with prostaglandin and ionizing radiation may first be subjected to the cytotoxic amount of ionizing radiation and subsequently have the subject administered the therapeutically effective amount of prostaglandin. Alternatively, administration of the therapeutically effective amount of prostaglandin may be administered to the subject prior to subjecting the neoplasm to the cytotoxic amount of ionizing radiation. Where the administration of the therapeutically effective amount of prostaglandin is either prior to or subsequent to subjecting the neoplasm to the cytotoxic amount of ionizing radiation, a skilled practitioner in the art can readily determine the amount of time between the administration of the therapeutically effective amount of prostaglandin and subjecting the neoplasm to the cytotoxic amount of ionizing radiation. This amount of time may be seconds, minutes, hours, days, weeks, and so on. Alternatively, the therapeutically effective amount of prostaglandin may be administered concurrently to subjecting the neoplasm to the cytotoxic amount of ionizing radiation.

These alternative treatment strategies are likewise applicable to the method of increasing the ionizing radiation's cytotoxic effect on a neoplasm in a subject, the method of reducing the therapeutically effective amount of ionizing radiation needed to treat a neoplasm in a subject, and the method of screening a prostaglandin compound's capacity to increase ionizing radiation's cytotoxic effect on neoplastic cells.

In another aspect, the invention relates to a method of treating a neoplasm in a subject, comprising administering a therapeutically effective amount of prostaglandin to the subject, and subjecting the neoplasm to a cytotoxic amount of ionizing radiation, thereby treating the neoplasm, where the prostaglandin is administered with a pharmaceutically acceptable carrier.

Depending on whether the prostaglandin is administered orally, parenterally, or otherwise, the administration of the prostaglandin can be in the form of solid, semi-solid, or liquid dosage forms, such as, for example, tablets, pills, capsules, powders, liquids, creams, and suspensions, or the like, preferably in unit dosage form suitable for delivery of a precise dosage. The prostaglandin will include, as noted above, an effective amount of the selected prostaglandin in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing unacceptable biological effects or interacting in an unacceptable manner with the prostaglandin. Actual methods of preparing such dosage forms are known, or will be apparent, to those skilled in this art; for example, see *Remington's Pharmaceutical Sciences*, latest edition (Mack Publishing Co., Easton, Pa.).

In another aspect, the invention provides a method of treating a neoplasm in a subject, comprising administering a therapeutically effective amount of prostaglandin and administering a therapeutically effective amount of a platinum-based anti-tumor agent to the subject, wherein the therapeutically effective amount of the platinum-based anti-tumor agent is less than 60 mg/meter$^2$.

These platinum-based anti-tumor agents include all platinum-based antitumor agents. These include, but are not limited to, for example, cisplatin (cis-diamminedichloroplatinum), and carboplatin (cis-diammine[1,1-cyclobutane-dicarboxylato] platinum). A skilled practitioner in the art will appreciate the wide variety of platinum-based anti-tumor agents available to treat neoplastic cells.

A skilled practitioner in the art can also readily determine a therapeutically effective amount of these platinum-based anti-tumor agents. The exact dose will, of course vary, and will depend on such factors as the subject's age, the subject's health, the subject's weight, the neoplastic condition being treated, the extent of the neoplastic condition being treated, and so on.

The administration of the platinum-based anti-tumor agent can be as a single administration or multiple administrations. Where the administration is a single administration, the amount of platinum-based anti-tumor agent administered can range from about 1 mg/meter$^2$ (body surface area) to about 80 mg/meter$^2$. In another embodiment, the amount of platinum-based anti-tumor agent administered can range from about 1 mg/meter$^2$ to about 60 mg/meter$^2$; in another embodiment, the amount of platinum-based anti-tumor agent administered can range from about 4 mg/meter$^2$ to about 60 mg/meter$^2$; and in another embodiment, the amount of platinum-based anti-tumor agent administered can range from about 4 mg/meter$^2$ to about 40 mg/meter$^2$; in another embodiment. In a prefered embodiment, the amount of platinum-based anti-tumor agent administered is less than 60 mg/meter$^2$. Even more preferably, the amount of platinum-based anti-tumor agent administered can range from about 8 mg/meter$^2$ to about 10 mg/meter$^2$.

Where the administrations are multiple and over a period of time, the amount of platinum-based anti-tumor agent administered can range from about 1 mg/meter$^2$/month (body surface area) to about 80 mg/meter$^2$/month. In another embodiment, the amount of platinum-based anti-tumor agent administered can range from about 1 mg/meter$^2$/ month to about 60 mg/meter²/month; in another embodiment, the amount of platinum-based anti-tumor agent administered can range from about 4 mg/meter²/month to about 60 mg/meter²/month; and in another embodiment, the amount of platinum-based anti-tumor agent administered can range from about 4 mg/meter²/month to about 40 mg/meter²/month; in another embodiment. In a prefered embodiment, the amount of platinum-based anti-tumor agent administered is less than 60 mg/meter²/month. Even more preferably, the amount of platinum-based anti-tumor agent administered can range from about 8 mg/meter²/month to about 10 mg/meter²/month.

Actual methods of administering such therapeutically effective amounts of a platinum-based anti-tumor agent are known, or will be apparent, to those skilled in the art; for example, see *Cancer: Principles and Practice of Oncology*, by DeVita, et al. Depending on whether the platinum-based anti-tumor agent is administered orally, parenterally, or otherwise, the administration of the platinum-based anti-tumor agent can be in the form of solid, semi-solid, or liquid dosage forms, such as, for example, tablets, pills, capsules, powders, liquids, creams, and suspensions, or the like, preferably in unit dosage form suitable for delivery of a precise dosage. The platinum-based anti-tumor agent may include an effective amount of the selected platinum-based anti-tumor agent in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing unacceptable biological effects or interacting in an unacceptable manner with the platinum-based anti-tumor agent. Actual methods of preparing such dosage forms are known, or will be apparent, to those skilled in this art; for example, see *Remington's Pharmaceutical Sciences*, latest edition (Mack Publishing Co., Easton, Pa.).

The neoplasm in a subject being treated with prostaglandin and a platinum-based anti-tumor agent may first be administered the platinum-based anti-tumor agent and subsequently have the subject administered the therapeutically effective amount of prostaglandin. Alternatively, the therapeutically effective amount of prostaglandin may be administered to the subject prior to the administration of the platinum-based anti-tumor agent. Where the administration of the therapeutically effective amount of prostaglandin is either prior to or subsequent to administering to the subject a platinum-based anti-tumor agent, a skilled practitioner in the art can readily determine the amount of time between the administration of the therapeutically effective amount of prostaglandin and the administration of the platinum-based anti-tumor agent. This amount of time may be seconds, minutes, hours, days, weeks, and so on. Alternatively, the therapeutically effective amount of prostaglandin may be administered concurrently to the administration of the platinum-based anti-tumor agent.

Utility

The present invention has many useful and practical utilities as noted herein. For example, the present invention provides for a method of treating a neoplasm in a subject by administering to the subject a therapeutically effective amount of prostaglandin and subjecting the neoplasm to a cytotoxic amount of ionizing radiation. Alternatively, the present invention provides for a method of reducing the therapeutically effective amount of ionizing radiation required to treat a neoplasm in a subject by administering to the subject a therapeutically effective amount of prostaglandin prior to subjecting the neoplasm to a reduced therapeutically effective amount of ionizing radiation.

The following example is put forth so as to provide those of ordinary skill in the art with a complete disclosure and description of how the methods claimed herein are utilized and evaluated, and is intended to be purely exemplary of the invention and is not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. and pressure is at or near atmospheric.

EXAMPLES

Introduction

It was previously demonstrated that tamoxifen (TAM) and cisplatin (DDP) are synergistic in a variety of human malignant cell lines including: melanoma (T-289), small cell lung cancer (UMC-5) and ovarian cancer (2008) (1). Additionally, TAM interferes with the ability of tumor cells to develop resistance to DDP (2). In examining the mechanism of TAM/DDP synergy, we have demonstrated that synergy is not related to an effect of TAM on DDP accumulation, intracellular levels of metallothionein IIa or glutathione, or on the formation or repair of DDP-DNA adducts (1). Similarly, it is not dependent upon the presence of estrogen receptors, a change in the activity or amount of calmodulin or anti-Protein Kinase C activity (1). It is dependent upon a TAM "effect" as resistance to TAM abolishes synergy while DDP resistance can be overcome by increasing the concentration of TAM in the system (1).

It is commonly recognized that all of the cytotoxic effects of TAM cannot be explained by simple blockade of the estrogen receptor. As an additional mechanism to explain the effects of TAM, Kiss has recently demonstrated that TAM stimulates the activity phospholipase D (3). Furthermore, Ishimoto et al. have demonstrated that an increase in phospholipase D is associated with an increase in the production of prostaglandin $D_2$ ($PG-D_2$) (4). $PG-D_2$ is the precursor for a series of inhibitory prostaglandins (PG) of which $\Delta^{12}$-Prostaglandin $J_2$ ($\Delta^{12}$-$PG\ J_2$) is one of the final metabolites (5). $PG-D_2$ and $\Delta^{12}$-$PG\ J_2$ have been shown to be cytotoxic in several different malignant cell lines (6–9). More recently Kim et al. have demonstrated that $\Delta^{12}$-$PG\ J_2$ induces apoptosis in LI210 leukemia cells (10). We have, therefore, hypothesized that TAM/DDP synergy is dependent upon the cell's ability to increase phospholipase D activity in response to TAM exposure. The increased activity of phospholipase D produces $PG-D_2$ with subsequent increase in the production of $\Delta^{12}$-$PG\ J_2$, which in turn synergizes with DDP.

To confirm this hypothesis, we first sought to determine the cytotoxicity of $\Delta^{12}$-$PG\ J_2$ in malignant cells and then to determine whether or not it is synergistic with DDP.

Materials and Methods

Cell Lines and Cell Culture

The T-289 cells were obtained from a patient with metastatic melanoma and carried in culture for 8 years (11). The 289 $TAM_{(6)}$ and 289 $DDP_{(3)}$ cell lines are variant T-289 melanoma cells that are 8-fold TAM resistant and 9-fold DDP resistant respectively, which we have developed in our laboratory (1). The UMC-5 small cell lung cancer line was obtained from Steve Grazziano, M.D., while the DLD colon, LnCAP-1 prostate and CAPAN-1 pancreatic cancer cell lines were obtained from Dennis Watson, Ph.D. The 2008 and C-13* ovarian cancer lines were obtained from Stephen B. Howell, M.D. The MCF-7 (estrogen receptor [ER] positive) and HTB- 126 (ER negative) breast cancer lines were obtained from the American Type Culture Collection (ATCC).

The melanoma and the UMC-5 cell lines were cultured in RPMI 1640 supplemented with 5% fetal calf serum (FCS), 50 $\mu$g/ml gentamicin, 2 mM L-glutamine, 10 nM hydrocortisone, 5 $\mu$g/ml insulin, 5 $\mu$g/ml human transferrin, 10 mM estradiol and 5 ng/ml selenium. The DLD- 1 cells were cultured in RPMI 1640 supplemented with 10% FCS and gentamicin while the CAPAN-1 an LnCAP-1 lines were cultured similarly in 15% FCS. The MCF-7 and HTB-126 lines were cultured in Dulbeccos Modified Eagles Media (DME) supplemented with 10% FCS, Na-pyruvate, non-essential amino acids and gentamicin.

Drugs and Chemicals

DDP (Platinol) clinical grade was obtained from Bristol Myers, Squibb (Evansville, Ind.); $\Delta^{12}$-PG $J_2$ (Prosta-5,9,12-trien-1-olic acid, 15-hydroxy- 11-oxo-) was obtained from Cayman Chemicals (Ann Arbor, Mich.); Sea Plaque low temperature-melting agarose was obtained from FMC Bio-Products (Rockland, Me.).

Colony Forming Assay (CFA)

CFA's for all melanoma, UMC-5 and LnCAP cell lines were performed in soft agar. Cells were cultured in 75 cm² tissue culture flasks (Corning, Corning, N.Y.), trypsinized, washed in media and then counted. The appropriate number of cells (4,000 cells/ml) was then added to 15 ml tubes containing 0.2% low temperature-melting agarose at 37° C. and either DMSO (control) or the appropriate concentration of $\Delta^{12}$-PG $J_2$ in DMSO. The DMSO concentration in all systems was kept below 0.1%. The cell suspension was well mixed and then aliquoted at 1 ml/dish in triplicate onto preprepared 35 mm dishes containing a basement layer of solidified 1% agarose. The cell-containing layer was allowed to solidify at room temperature and the dishes were then placed in an incubator at 37° C. and 5% $CO_2$. Colonies greater than 125 $\mu$m were counted after 7 (melanoma, LnCAP) and 14 (UMC-5) days.

All other CPA's were performed on plastic 60 mm culture dishes. For these studies the appropriate number of cells was placed in 5 ml of medium, specific for the cell type. The cells were incubated at 37° C. in 5% $CO_2$ for 7 days. On day 7, the media was removed, the colonies were washed with PBS, fixed with methyl alcohol and stained using Giemsa stain. After staining, the visible colonies (containing>50 cells) were counted.

For CFA's involving ionizing radiation, the cells were suspended in appropriate medium and transported to the Radiation Therapy Department on ice, where they were exposed to the prescribed dose of radiation using a SHM Nuclear Therapi 4 Linac, generating 4 Mv X-rays at a dose rate of 5 Gy/2.7 min. The cells were then returned to the laboratory and seeded onto culture dishes as described above.

Median Effect Analysis

Median effect analysis (MEA) was used to determine the nature of the interaction between $\Delta^{12}$-PG $J_2$ and either DDP or radiation (XRT) (12). The combination index (CI) was determined from colony-forming assays at increasing levels of cell kill. CI values of less than or greater than 1 indicate synergy or antagonism, respectively, whereas a CI value of 1 indicates additivity of the treatments. Either the drugs or radiation were combined at a ratio equal to their 50% inhibitory concentration ($IC_{50}$) values as determined by clonagenic assay. As a control, in every experiment, the combination was compared to the cytotoxicity of each treatment alone.

Results

Colony Forming-Assays $\Delta^{12}$-PG $J_2$ proved to be cytotoxic to a wide variety of malignancies (Table 1). The highest $IC_{50}$ values were obtained using the 289 $DDP_3$ and LnCAP cell lines (3.3±0.45 $\mu$M SD and 3.12±0.15 $\mu$M respectively) while the lowest $IC_{50}$ was with the UMC-5 small cell lung cancer line (0.70 $\mu$M).

TABLE 1

$\Delta^{12}$-PG $J_2$ CYTOTOXICITY

| CELL LINE | $IC_{50}$ ($\mu$m) |
|---|---|
| T-289 | 1.30 |
| 289DDP₃ | 3.30 |
| 289 TAM₆ | 1.03 |
| DLD | 1.74 |
| CAPAN-1 | 1.87 |
| LNCAP | 3.12 |
| UMC-5 | 0.70 |
| MCF-7 | 1.30 |
| HTB-126 | 1.30 |
| 2008 | 0.84 |
| C-13* | 1.0 |

The $IC_{50}$ values for the 289 and 289 TAM₆ in melanoma cell lines were similar (1.30 $\mu$M±0.71 and 0.87 $\mu$M±0.23 SD respectively). Thus, TAM resistance did not appear to have any effect on $\Delta^{12}$-PG $J_2$ sensitivity. In contrast, the DDP resistant variant 289 DDP₃ had an $IC_{50}$ (3.3±0.45 $\mu$M SD) that was approximately 2.5-fold higher than the parental T-289.

In order to more clearly determine the effect of DDP resistance on the sensitivity to $\Delta^{12}$-PG $J_2$, we evaluated the cytotoxicity of $\Delta^{12}$-PG $J_2$ in the 2008 ovarian cancer cell line and it's DDP resistant variant C-13*. The $IC_{50}$ for both of these cell lines was comparable (0.84 $\mu$M±0.33 SD and 1.0 $\mu$M±0.25, respectively); therefore, DDP resistance does not universally confer resistance to $\Delta^{12}$-PG $J_2$.

In a similar manner, the $IC_{50}$'s for the MCF-7 (TAM sensitive, ER +), and the HTB-126 (TAM resistant, ER−) breast cancer cell lines had essentially identical $IC_{50}$'s (1.30±0.47 SD and 1.30±0.10 SD respectively). The mechanism of TAM resistance in the HTB-126 is based upon loss of the ER, whereas the mechanism of resistance in the 289 TAM₆ cell line is unknown but appears to be related to the loss of high affinity anti-estrogen binding sites from the nucleus of the cell.

The $IC_{50}$'s for the DLD and CAPAN-1 cells lines, which are adenocarcinomas of gastrointestinal origin, were similar (1.74 $\mu$M±0.73 SD and 1.87 $\mu$M±0.94 SD respectively), while the $IC_{50}$ for the LnCAP cell line, which is an adenocarcinoma of prostatic origin, was 3.12 $\mu$M±0.15 SD. The UMC-5 small cell lung cancer cell line which is of neural crest origin, similar to melanoma, was quite sensitive ($IC_{50}$ of 0.70 $\mu$M).

Median Effect Analysis $\Delta^{12}$-PG $J_2$ DDP

We investigated the nature of the interaction between $\Delta^{12}$-PG $J_2$ and DDP in the melanoma cell lines, to determine if the two drugs interact in a synergistic manner. We first examined the interaction in the parent cell line T-289. The CI$_{50}$ for the interaction was 0.72 indicating that the interaction is synergistic in nature. The CI$_{50}$ for this interaction was higher than that which we obtained for TAM/DDP synergistic interactions (CI$_{50}$=0.26).

We also investigated the interaction of $\Delta^{12}$-PG J$_2$/DDP in the 289 TAM$_6$ cell line to determine the effect of TAM resistance. As can be seen in FIG. 1, there is significant synergy associated with this interaction. The CL$_{50}$ for this cell line is 0.17. This interaction remained synergistic, despite the fact that the cell was TAM-resistant. In contrast, the development of TAM resistance resulted in a loss of synergy between TAM and DDP in this same cell line (1). This was predictable based upon the CFA data which demonstrated that the 289 TAM$_6$ was very sensitive to $\Delta^{12}$-PG J$_2$ and gives further evidence that TAM resistance has no effect on cytotoxic action of $\Delta^{12}$-PG J$_2$.

$\Delta^{12}$-PG J$_2$. XRT

We hypothesized, that since DDP and XRT both induce DNA damage and initiate the apoptotic pathway, similar synergy between $\Delta^{12}$-PG J$_2$ and XRT might exist and be of potential clinical importance. In order to make the conditions of the experiment as close to the potential clinical situation as possible, we used the same radiation machine that is used in the treatment of patients. The dose rate of the XRT exposure is also identical to that used for patients.

Figure 2:
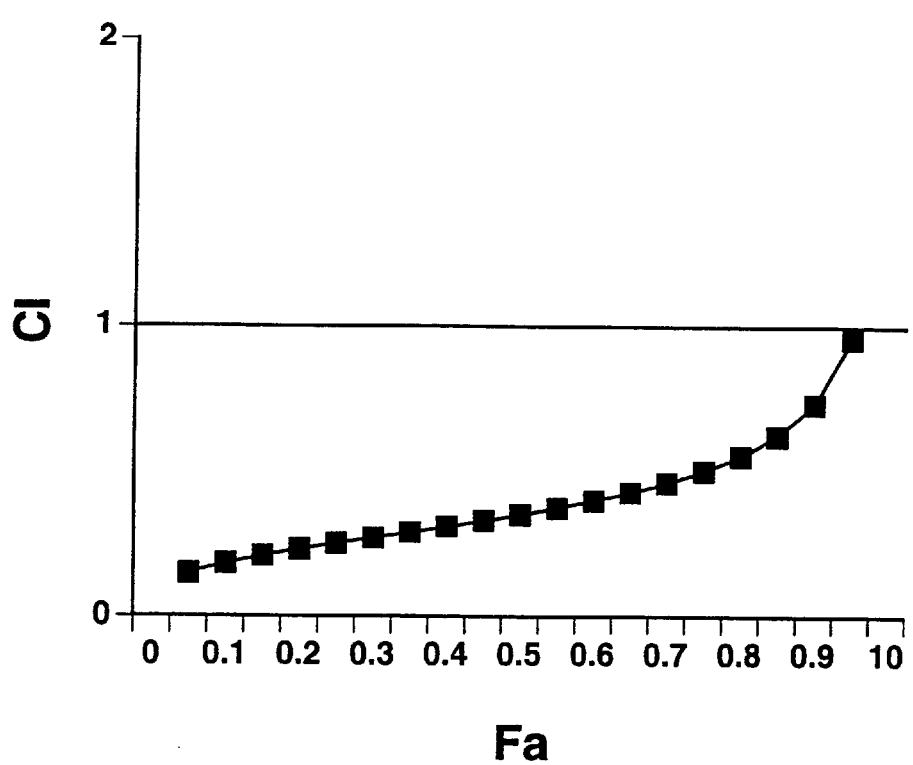
FIG. 2 shows the median effects analysis plot of the interaction between $\Delta^{12}$-PG J$_2$ and ionizing radiation (XRT) in the human melanoma cell line T-289. Fa=the fraction affected (the fraction of cells killed by $\Delta^{12}$-PG J$_2$). CI=the combination index (the interaction between $\Delta^{12}$-PG J$_2$ and XRT; CI values above 1 indicate an antagonistic effect, CI values=1 indicate an additive effect, and CI values below 1 indicate a synergistic effect).

We first explored the synergistic interaction in the T-289 melanoma cell line. In this experiment the cells are irradiated first and then cultured continuously in $\Delta^{12}$-PG J$_2$. As can be seen in FIG. 2, a significant synergistic cytotoxic interaction is evident with a CI$_{50}$ of 0.35. In the presence of 150 nM $\Delta^{12}$-PG J$_2$, the IC$_{50}$ for XRT decreases from 200 cGy to 50 cGy. Likewise, the IC$_{50}$ for $\Delta^{12}$-PG J$_2$ fall from 1.30 µM to 150 nM when the cells are exposed to 50 cGy.

As we had demonstrated that TAM/DDP synergy was not restricted to melanoma but present also in ovarian and small cell lung cancer lines, we investigated to which extent $\Delta^{12}$-PG J$_2$ and XRT synergy existed in other types of malignancies.

Figure 3:
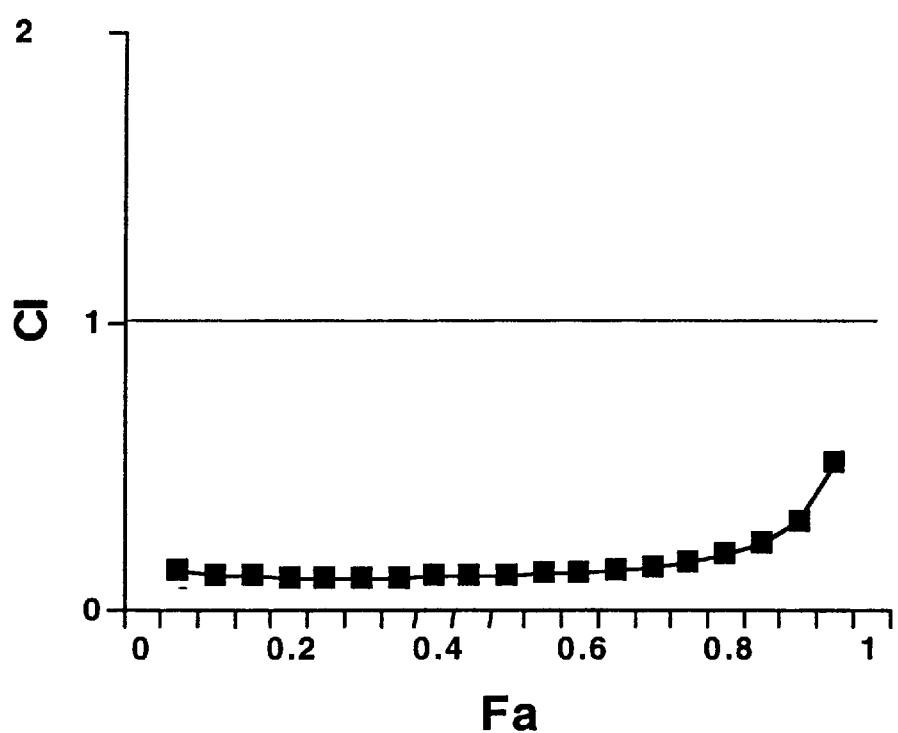
FIG. 3 shows the median effects analysis plot of the interaction between $\Delta^{12}$-PG J$_2$ and ionizing radiation (XRT) in the human prostate cancer cell line LnCAP. Fa=the fraction affected (the fraction of cells killed by $\Delta^{12}$-PG J$_2$). CI=the combination index (the interaction between $\Delta^{12}$-PG J$_2$ and XRT; CI values above 1 indicate an antagonistic effect, CI values=1 indicate an additive effect, and CI values below 1 indicate a synergistic effect).

In light of the important role for XRT in the patients with prostate cancer, we first investigated the $\Delta^{12}$-PG J$_2$/XRT interaction in the LnCAP-1 prostate cancer line. As can be seen in FIG. 3, remarkable synergy was present as evidenced by the CI$_{50}$ value of 0.12. This represents the most synergistic interaction that we have found thus far. In the presence of only 375 nM $\Delta^{12}$-PG J$_2$, the IC$_{50}$ for XRT falls from 200 cGy to<25 cGy. This should have significant clinical implications.

We have further studied this interaction and determined that $\Delta^{12}$-PG J$_2$/XRT synergy exists in the 2008 ovarian cell line (CI$_{50}$=0.72), while in the DLD, CAPAN-1 and HTB-126 cell lines the interaction is minimally synergistic or additive.

Discussion

In this study, we have demonstrated for the first time, that a synergistic cytotoxic interaction is present between $\Delta^{12}$-PG J$_2$ and both DDP and XRT. This synergistic interaction is manifest in a variety of different malignant cell lines, establishing the fact that synergy is not confined to any one particular cell type.

$\Delta^{12}$-PG J$_2$ is a metabolite of PG-D$_2$, a PG with demonstrable inhibitory actions in malignant melanoma as well as other malignant cell lines (6,8,13). The inhibitory actions of this PG were first identified by Stringfellow and Fitzpatrick, who were evaluating the metastatic potential of two murine melanoma cell lines, B16F, parental and B 16F$_{10}$, a variant with increased metastatic potential (6,13). The authors demonstrated that the parental cells metastasized at a rate less than half that of the variant line, while producing more than 5 times the amount of PG-D$_2$ (13). They subsequently demonstrated that pretreatment of the parental B16F$_1$ with indomethacin, an inhibitor of PG production, resulted in a statistically significant increase in the number of metastases, comparable to that of the variant B16F$_{10}$ (6). Additionally, treatment of the B16F$_{10}$ line with PG-D$_2$ resulted in a marked decrease in the number of metastases.

As work with PG-D$_2$ continued, it became apparent that the major inhibitory effects of this compound were actually mediated by metabolites 9-deoxy-$\Delta^9$ PG-D$_2$ (PG J$_2$) and subsequently 9-deoxy-$\Delta^{12}$PG-D$_2$ ($\Delta^{12}$ PG J$_2$) (14,15). Fitzpatrick and Wynalda also demonstrated that, in the presence of albumin, PG-D$_2$ underwent a series of dehydration steps which produced among other metabolites, the $\Delta^{12}$-PG J$_2$ compound (16). In a series of elegant experiments, Narumiya and Fukushima demonstrated that the inhibitory effects of PG-D$_2$ were due almost completely to the $\Delta^{12}$-PG J$_2$ metabolite (5). Using the murine leukemia cell line L-1210, they demonstrated that a constant 24 hr exposure to PG-D$_2$ was required before cytotoxicity was observed. In contrast, with $\Delta^{12}$-PG J$_2$, cytotoxicity was observed in as little as 6 hours and the concentration required was less than 50% that of the PGD$_2$. They then showed that within 24 hours PG-D$_2$ was metabolized almost completely to $\Delta^{12}$-PG J$_2$. Finally, they showed that replacing the PG-D$_2$ containing media every 6 hours prevented the build up of the metabolites and also significantly reduced the cytotoxicity of the parent compound. Thus, this evidence strongly supports the possibility that in human serum, PG-D$_2$ is metabolized to $\Delta^{12}$-PG J$_2$ which in turn is responsible for the cytotoxic properties of these agents.

The exact mechanism by which PG's exert their antiproliferative function is unclear, however, there have been more recent studies that provide important clues. Several investigators have demonstrated that the treatment of tumor cells with PG's of the A and J series is associated with an arrest of growth in the G$_0$/G$_1$ phase of the cell cycle and the induction of heat shock proteins (HSP) (17–21). This induction is not observed with PG's that are not antiproliferative. PGA$_2$ has been shown to increase the expression of GADD 153 MRNA (22). Expression of the GADD 153 gene has been associated with growth arrest and DNA damage; moreover this gene is a member of a group of at least 5 genes with similar properties (23). The induction of GADD 153 expression correlated with the length of exposure to PGA$_2$. The expression of GADD 153 was dependent upon transcription and partially blocked by protein synthesis inhibition.

More recently both PGA$_2$ and $\Delta^{12}$-PG J$_2$ have been shown to induce apoptosis in L1210 leukemia cells (10). Kim et al. have shown that cytotoxic concentrations of both prostaglandins resulted in the morphologic changes associated with apoptosis, resulting in the production of internucleosomal DNA strand breaks. Concentrations of $\Delta^{12}$-PG J$_2$ of 1 mg/ml were found to be growth inhibitory; however, 2 mg/ml was cytotoxic. In contrast to the studies of Bhuyan et al. and Sasaguri et al. showing an arrest at the G$_0$G$_1$ phase of the cell cycle, Kim's data demonstrated that six hours after exposure to $\Delta^{12}$-PG J$_2$ ($\leq$2 mg/ml), cells arrested at the G$_2$/M phase of the cell cycle (10,17,18). By 24 hr, DNA fragmentation was evident and accurate evaluation of the cell cycle was not possible. Consistent with the apoptotic response that requires protein synthesis, 0.5 mg/ml of cycloheximide administered 1 hour before the addition of $\Delta^2$-PG J$_2$ completely blocked DNA fragmentation. This evidence is consistent with a model wherein exposure of tumor cells to $\Delta^{12}$-PG J$_2$ results in an arrest at the G$_2$/M phase of the cell cycle, ultimately resulting in cell death via an apoptotic mechanism.

The parent compound, PG-D$_2$, has been given to normal volunteers and has resulted in a mild decrease in the systemic blood pressure with associated tachycardia, facial flushing and nasal congestion (24). This is consistent with the known vasoactive effects of this PG in patients with systemic mastocytosis, a disease associated with disordered PG-D$_2$ production. It is expected that $\Delta^{12}$-PG J$_2$ may produce less symptomatology in patients as $\Delta^{12}$-PG J$_2$ has less in the way of vasoactive properties than the parent compound (15). Additionally, as it is found in the urine of normal individuals, it is likely the final metabolite and therefore potentially more stable in human serum (25). In further support of the potential of this agent for human use, Nishimura has demonstrated that nude mice tolerated up to 30 mg/kg of $\Delta^{12}$-PG J$_2$ with no change in the body weights of the animals and no toxic effects on the liver or kidney (26).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the following claims.

Throughout this application various publications are referenced by numbers within parentheses. Full citations for these publications are are follows. The disclosures of these publications in their entireties are hereby incorporated by reference into this application in order to more fully describe the state of the art to which this invention pertains.

REFERENCES

1. McClay, E. F., Albright, K. A., Jones, J. A., Christen, R., and Howell, S. B. Tamoxifen modulation of cisplatin sensitivity in human malignant melanoma cells. *Cancer Res.*, 53: 1571–1576, 1993.
2. McClay, E. F., Albright, K. A., Jones, J. A., Christen, R., and Howell, S. B. Tamoxifen delays the development of resistance to cisplatin in human malignancies. *Br. J Cancer*, 70: 449–452, 1994.
3. Kiss, Z. Tamoxifen stimulates phospholipase D activity by an estrogen receptor-independent mechanism. *Fed Europ Biochem Soc*, 355: 173–177, 1994.
4. Ishimoto, T., Akiba, S., Sato, T., and Fujii, T. Contribution of phospholipase A$_2$ and D to arachidonic acid liberation and prostaglandin D$_2$ formation with increase in intracellular Ca$^{2+}$ concentration in rat peritoneal mast cells. *E. J. Biochem.*, 219: 401–406, 1994.
5. Narumiya, S. and Fukushima, M. $\Delta^{12}$-prostaglandin J$_2$, an ultimate metabolite of prostaglandin D$_2$ exerts cell growth inhibition. *Biochem. Biophy. Res. Comm.*, 127: 739–745, 1985.
6. Stringfellow, D. A. and Fitzpatrick, F. A. Prostaglandin D$_2$ controls metastasis of malignant melanoma cells. *Nat.*, 282: 76–78, 1979.
7. Simmet, T. and Jaffe, B. M. Inhibition of B-16 melanoma growth in vitro by prostaglandin D$_2$. *Prostaglandins*, 25: 47–54, 1983.
8. Kikuchi, Y., Myiauchi, M., Oomori, K., Kita, T., Kizawa, I., and Kato, K. Inhibition of ovarian cancer cell growth in vitro and in nude mice by prostaglandin D$_2$ *Cancer Res.*, 46: 3363–3366, 1986.
9. Kato, T., Fukushima, M., Kurozumi, S., and Noyri, R. Antitumor activity of $\Delta^7$-prostaglandin A$_1$, and $\Delta^{12}$-prostaglandin J$_2$ in vitro and in vivo. *Cancer Res.*, 46: 3538–3542, 1986.
10. Kim, I. K., Lee, J. H., Sohn, H. W., Kim, H. S., and Kim, S. H. Prostaglandin A2 and $\delta^{12}$-prostaglandin J$_2$ induce apoptosis in L1210 cells. *Fed Europ Biochem Soc*, 321: 209–214, 1993.
11. Taetle, R., Jones, O., Honeysett, J., Abramson, I., Bradshaw, C., and Reid, S. Characterization of xenograft-derived melanoma cell lines. *Cancer*, 60: 1836–1841, 1987.
12. Chou, T. C. and Talalay, P. Quantitative analysis of dose-effect relationships: the combined effects of multiple drugs or enzyme inhibitors. *Adv. Enzyme Reg*, 22: 27–55, 1986.
13. Fitzpatrick, F. A. and Stringfellow, D. A. Prostaglandin D$_2$ formation by malignant melanoma cells correlates inversely with cellular metastatic potential. *Proc. Natl. Acad Sci.*, 76: 1765–1769, 1979.
14. Kikawa, Y., Narumiya, S., Fukushima, M., Wakatsuka, H., and Hayaishi, O. 9-Deoxy-$\Delta^9$, $\Delta^{12}$. 3,14-dihydroprostaglandin D$_2$, a metabolite of prostaglandin D$_2$ formed in human plasma. *Proc. Natl. Acad. Sci.*, 81: 1317–1321, 1984.
15. Fukushima, M., Kato, T., Ota, K., Arai, Y., Narumiya, S., and Hayaishi, O. 9-deoxy-$\Delta^9$-prostaglandin D$_2$, a prostaglandin D$_2$, derivative with potent antineoplastic activity and weak smooth muscle-contracting activities. *Biochem. Biophy. Res. Comm.*, 109: 623–633, 1982.
16. Fitzpatrick, F. A. and Wynalda, M. A. Albumin catalyzed metabolism of prostaglandin D$_2$: Identification of products formed in vitro. *J. Biol. Chem.*, 258: 11713–11718, 1983.
17. Bhuyan, B. K., Adams, E. G., Badiner, G. J., Li, L. H., and Barden, K. Cell cycle effects of Prostaglandins A$_1$, A$_2$ and D$_2$ in human and murine melanoma cells in culture. *Cancer Res.*, 46: 1688–1693, 1986.
18. Sasaguri, T., Masuda, J., Shimokada, K., Yokoto, T., Kosaka, C., Fujishima, M., and Ogata, J. Prostaglandins A and J arrest the cell cycle of cultured vascular smooth muscle cells without suppression of c-myc expression. *Exp. Cell Res.*, 200: 351–357, 1992.
19. Ohno, K., Fukushima, M., Fujiwara, M., and Naruniiya, S. Induction of 68,000 dalton heat shock proteins by cyclopentenone prostaglandins. *J. Bio. Chem.*, 263: 19764–19770, 1988.
20. Santoro, M. G., Garaci, E., and Amici, C. Prostaglandins with antiproliferative activity induce the synthesis of a heat shock protein in human cells. *Proc. Natl. Acad. Sci.*, 86: 8407–8411, 1989.
21. Santoro, M. G., Garaci, E., and Amici, C. Induction of heat shock protein synthesis by prostaglandins with antineoplastic and antiviral activity. *Adv. Prostaglandin Thromboxane Leukotriene Res.*, 21: 867–874, 1990.
22. Choi, A. M. K., Fargnoli, J., Carlson, S. G., and Holbrook, N. J. Cell growth inhibition by prostaglandin A$_2$ results in elevated expression of gadd 153 mRNA. *Exp. Cell Res.*, 199: 85–89, 1992.
23. Fornace, A. J., Nebert, D. W., Hollander, C., Luethy, L. D., Papathanasiou, M., Fargnoli, J., and Holbrook, N. J. Mammalian genes coordinately regulated by growth arrest signals and DNA-damaging agents. *Mol. Cell Bio.*, 9: 41906–44203, 1989.
24. Heavey, D. J., Lumley, P., Barrow, S. E., Murphy, M. E., Humphrey, P. P. A., and Dollery, C. T. Effects of intravenous infusions of prostaglandin D$_2$ in man. *Prostaglandins*, 28: 755–767, 1984.

25. Hirata, Y., Hayashi, H., Ito, S., Kikawa, Y., Ishibashi, M., Sudo, M., Miyazaki, M., Fukushhima, M., Narumiya, S., and Hayaishi, O. Occurrence of 9-deoxy $\Delta^9$, $\Delta^{12}$-13,14-dihydroprostaglandin $D_2$ in human urine. *J. Biol Chem.*, 263: 16619–16625, 1988.

26. Fukushima, M. Biological activities and mechanism of action of PG $J_2$ and related compounds: an update. *Prostagl. Leukotri. Essen. Fatty Acids*, 92: 471, 1992.

What is claimed is:

1. A method of treating a neoplasm in a subject wherein the neoplasm is sensitive to a synergistic combination of prostaglandin $D_2$ or $\Delta^{12}$-prostaglandin-$J_2$ and ionizing radiation, comprising:
   a. administering a synergistic therapeutically effective amount of prostaglandin $D_2$ or $\Delta^{12}$-prostaglandin-$J_2$ to the subject; and
   b. subjecting the neoplasm to a cytotoxic amount of ionizing radiation, thereby treating the neoplasm.

2. The method of claim 1, wherein the neoplasm is benign.

3. The method of claim 1, wherein the neoplasm is malignant.

4. The method of claim 1 wherein the treatment comprises halting the growth of the neoplasm.

5. The method of claim 1, wherein the treatment comprises killing the neoplasm.

6. The method of claim 1, wherein the treatment comprises reducing the size of the neoplasm.

7. The method of claim 1, wherein the amount of prostaglandin administered is from about 0.01 to 1000 μg/kg/day.

8. The method of claim 1, wherein the amount of prostaglandin is administered over about 1 to 10 days.

9. The method of claim 1, wherein the amount of prostaglandin administered is about 0.01 to 1000 μg/kg/day over about 1 to 10 days.

10. The method of claim 1, wherein the prostaglandin is administered with a pharmaceutically acceptable carrier.

11. The method of claim 1, wherein the step of subjecting the neoplasm to the radiation is performed within about the same day as the prostaglandin administration.

12. The method of claim 1, wherein the amount of ionizing radiation is a single dose of from about 5 to 200 cGy.

13. The method of claim 1, wherein the amount of ionizing radiation is a single dose of about 50 cGy.

14. The method of claim 1, wherein the neoplasm is a melanoma.

15. The method of claim 1, wherein the neoplasm is a melanoma, an adenocarcinoma, a malignant glioma, a prostatic carcinoma, a kidney carcinoma, a bladder carcinoma, a pancreatic carcinoma, a thyroid carcinoma, a lung carcinoma, a colon carcinoma, a rectal carcinoma, a brain carcinoma, a liver carcinoma, a breast carcinoma, or an ovarian carcinoma.

16. The method of claim 1, wherein the subject is a human.

17. The method of claim 1, wherein the neoplasm is selected from the group consisting of a melanoma, a malignant glioma, a prostatic carcinoma, a kidney carcinoma, a bladder carcinoma, a pancreatic carcinoma, a thyroid carcinoma, a lung carcinoma, a colon carcinoma, a rectal carcinoma, a brain carcinoma, a liver carcinoma, a breast carcinoma, and an ovary carcinoma.

18. A method of increasing ionizing radiation's cytotoxic effects on a neoplasm in a subject by increasing the neoplasm's sensitivity to ionizing radiation, wherein the neoplasm is sensitive to a synergistic combination of prostaglandin $D_2$ or $\Delta^{12}$-prostaglandin-$J_2$ and ionizing radiation, comprising:
   a. administering a synergistic therapeutically effective amount of prostaglandin $D_2$ or $\Delta^{12}$-prostaglandin-$J_2$ to the subject; and,
   b. subjecting the neoplasm to a therapeutically effective amount of ionizing radiation, thereby increasing the cytotoxic effects of the ionizing radiation on the neoplasm.

19. A method of reducing the therapeutically effective amount of ionizing radiation required to treat a neoplasm in a subject, compared to treating with ionizing radiation alone, wherein the neoplasm is sensitive to a synergistic combination of prostaglandin $D_2$ or $\Delta^{12}$-prostaglandin-$J_2$ and ionizing radiation, comprising:
   a. administering a synergistic therapeutically effective amount of prostaglandin $D_2$ or $\Delta^{12}$-prostaglandin-$J_2$ to the subject, thereby reducing the therapeutically effective amount of ionizing radiation required to treat the neoplasm in the subject, compared to treating with ionizing radiation alone; and,
   b. subjecting the neoplasm in the subject to the reduced therapeutically effective amount of ionizing radiation.

\* \* \* \* \*